United States Patent
Parekh et al.

(10) Patent No.: US 11,425,924 B2
(45) Date of Patent: Aug. 30, 2022

(54) COMPOSITION AND METHOD FOR CONTROLLED-RELEASE OF AMINO ACIDS

(71) Applicants: Gaurav Parekh, Twin Falls, ID (US); Brent L. Petersen, Twin Falls, ID (US)

(72) Inventors: Gaurav Parekh, Twin Falls, ID (US); Brent L. Petersen, Twin Falls, ID (US)

(73) Assignee: Glanbia Nutritionals, Ltd., Kilkenny (IE)

( * ) Notice: Subject to any disclaimer, the term of this patent is extended or adjusted under 35 U.S.C. 154(b) by 233 days.

(21) Appl. No.: 16/248,624

(22) Filed: Jan. 15, 2019

(65) Prior Publication Data

US 2019/0328023 A1 Oct. 31, 2019

Related U.S. Application Data

(60) Provisional application No. 62/617,586, filed on Jan. 15, 2018.

(51) Int. Cl.
| | |
|---|---|
| *A23L 33/175* | (2016.01) |
| *A23L 29/231* | (2016.01) |
| *A23L 29/25* | (2016.01) |
| *A61K 31/198* | (2006.01) |

(52) U.S. Cl.
CPC .......... *A23L 33/175* (2016.08); *A23L 29/231* (2016.08); *A23L 29/25* (2016.08); *A61K 31/198* (2013.01)

(58) Field of Classification Search
CPC ...... A23L 33/175; A23L 29/231; A23L 29/25; A61K 31/198
USPC .......................................................... 514/577
See application file for complete search history.

(56) References Cited

U.S. PATENT DOCUMENTS

| | | | |
|---|---|---|---|
| 5,952,007 A | 9/1999 | Bakker et al. | |
| 9,186,640 B2 * | 11/2015 | Kohane | A61K 9/0053 |

OTHER PUBLICATIONS

Gulao et al. (Food Chemistry, 2016, 194680-686) (Year: 2016).*
Schmitt, C. and Turgeon, S.L. Protein/polysaccharide complexes and coacervates in food systems, Advances in Colloid and Interface Science 167 (2011) 63-70, Elsevier B.V.
Gulao, E. et al. Complex coacervates obtained from peptide leucine and gum arabic: Formation and characterization interactions, Food Chemistry 194 (2016) 680-686), Elsevier B.V.
Livney, Y.D., Complexes and conjugates of biopolymers for delivery of bioactive ingredients via food, in Delivery and Controlled Release of Bioactives in Foods and Nutraceuticals (Nissim Garti, Editor), 2008, p. 234-250, CRC Press/Woodhead Publishing.

* cited by examiner

*Primary Examiner* — Yevgeny Valenrod
(74) *Attorney, Agent, or Firm* — Donna J. Russell

(57) ABSTRACT

Disclosed is an amino acid/soluble polysaccharide coacervate that provides modified release of amino acid in the digestive system. A method is also disclosed for forming amino acid coacervate compositions to provide increased delivery and release of one of more amino acids, such as leucine, for example, to the intestine of a human and/or animal.

16 Claims, 6 Drawing Sheets

COMPOSITION AND METHOD FOR CONTROLLED-RELEASE OF AMINO ACIDS

FIELD OF THE INVENTION

The invention relates to amino acid compositions which provide amino acids in more bioavailable forms. More specifically, the invention relates to compositions which provide improved delivery of non-polar amino acids for absorption in a human and/or animal body, and methods for making those compositions.

BACKGROUND OF INVENTION

Loss of muscle tissue often occurs as a result of aging, malnutrition, and catabolic diseases such as burns, sepsis, and cancer. Dietary protein supplementation may be beneficial, but supplementation with the essential amino acid leucine has been shown to be especially beneficial. Dietary leucine has, for example, recently been shown to suppress the rate of myofibrillar protein degradation and muscle weight loss in rats. Leucine also stimulates muscle protein synthesis and modulates the activity of various proteins involved in the control of mRNA translation. Leucine may stimulate protein synthesis directly or through its metabolite, α-ketoisocaproic acid. Leucine may stimulate translation either independently or by interaction with the mammalian target of rapamycin (mTOR).

Leucine is a branched-chain amino acid, and an essential amino acid. It is the only amino acid that is converted to acetyl-coenzyme A and alpha-keto acids, and is an important source of nitrogen for synthesis of glutamine. In addition to its effects on protein synthesis and degradation, leucine also stimulates glucose uptake by protein kinase C (PKC), while insulin modulates glucose uptake via protein kinase B.

Whey proteins are a good source of leucine, but for many individuals who need the muscle-building amino acids dietary proteins can provide, it can be difficult to digest and/or absorb proteins. Furthermore, even for individuals who have normal digestion/absorption, Leucine (L-Leucine), being a non-polar amino acid with low solubility in water (24.3 mg/ml, except at very acidic pH) presents delivery and bioavailability issues. Because the solubility of leucine is pH-dependent, it tends to be released from pharmaceutical carriers or molecular complexes much more rapidly in the stomach (where the pH ranges from about 1 to 4.5 based on the type and volume of food eaten), but significantly more slowly in the small intestine (where the pH is about 6 in the duodenum and gradually increases to about 7.4 in the terminal ileum), where absorption into the bloodstream would actually take place. It is therefore important to find ways to provide leucine-containing amino acid compositions that provide those amino acids in a more bioavailable form which would decrease the release rate in the stomach and increase it in the intestine.

Various methods have been used for delivery of leucine which, being a non-polar amino acid, presents some challenges when formulating compositions for efficient delivery. For example, one approach has been to disperse leucine in water at or near neutral pH. Various encapsulating agents have also been used, including, for example, gum acacia in combination with at least one other agent such as sucrose fatty acid ester (i.e., sugar esters) and/or sodium carboxymethyl starch. Hydrolyzed whey protein has also been used to encapsulate L-leucine.

The recommended daily dosage of leucine is about 63 mg/kg body weight (http://www.cdc.gov/nchs/data/nhanes/databriefs/adultweight.pdf). For an average healthy male that should be about 4.032 g/day. Delivery of effective amounts of leucine in bioavailable form can be particularly important for athletes, older individuals, and individuals who have difficulty absorbing nutrients. What are needed are new and better ways of delivering amino acids—especially non-polar amino acids such as leucine. There is also a great need for delivery vehicles that target those amino acids to the intestine for greater absorption.

SUMMARY OF INVENTION

The invention relates to a composition comprising a coacervate consisting essentially of one or more amino acids (i.e., at least one amino acid) and at least one soluble polysaccharide. While the composition may contain additional ingredients such as food ingredients, flavorings, vitamins, minerals, for example, the coacervate within the composition will consist essentially of at last one amino acid and at least one soluble polysaccharide. In various aspects of the invention, the amino acid is non-polar. In various aspects of the invention, the amino acid is L-leucine. In various aspects of the invention, the at least one soluble polysaccharide is gum acacia. In various embodiments of the invention, the coacervate comprises from about 45 to about 50 percent amino acid, by weight of the coacervate. A leucine/soluble polysaccharide coacervate of the invention, for example, provides a modified-release leucine composition that provides increased leucine delivery to the human and/or animal intestine.

The invention also relates to a method for making a composition comprising an amino acid/soluble polysaccharide coacervate, the method comprising (a) dissolving at least one amino acid in water, adjusted to a pH of from about 1.0 to about 1.1, to produce an amino acid solution; (b) admixing at least one soluble polysaccharide with the amino acid solution, to produce an amino acid/polysaccharide admixture; and (c) adjusting the pH of the amino acid/polysaccharide admixture to from about 2.3 to about 2.5 to produce an amino acid/polysaccharide coacervate. In various aspects of the invention, a powdered amino acid/soluble polysaccharide modified delivery composition can be formed by adding a step of (d) drying the amino acid/polysaccharide coacervate. In various embodiments of the method, the at least one soluble polysaccharide is selected from the group consisting of gum acacia, pectin, soy-soluble polysaccharides, pea-soluble polysaccharides, and combinations thereof.

In various aspects, a method for making a composition comprising an amino acid/soluble polysaccharide coacervate comprises the steps of (a) dissolving at least one soluble polysaccharide in water which has been preheated to from about 110 to about 122 degrees Fahrenheit and adjusted to a pH of from about 1.0 to about 1.5, to produce a soluble polysaccharide solution; (b) admixing at least one amino acid into the soluble polysaccharide solution, to produce an amino acid/polysaccharide admixture; and (c) adjusting the pH of the amino acid/polysaccharide admixture to from about 2.4 to about 3.1 to produce an amino acid/polysaccharide coacervate.

In various aspects, the method for making a composition comprising an amino acid/soluble polysaccharide coacervate comprises the steps of (a) dissolving at least one amino acid in water, adjusted to a pH of from about 1.0 to about 1.5, to produce an amino acid solution; (b) heating the amino acid solution to a temperature of from about 110 to about 122 degrees Fahrenheit; (c) admixing at least one soluble polysaccharide into the heated amino acid solution to produce an amino acid/polysaccharide admixture; and (d) adjusting the pH of the amino acid/polysaccharide admixture to from about 2.4 to about 3.1 to produce an amino acid/polysaccharide coacervate.

In various aspects, the method further comprises a step of drying the amino acid/polysaccharide coacervate. In various aspects, the at least one soluble polysaccharide is selected from the group consisting of gum acacia, pectin, soy-soluble polysaccharides, pea-soluble polysaccharides, and combinations thereof. In various aspects, the at least one soluble polysaccharide is gum acacia. In various aspects, the at least one amino acid is non-polar, in some embodiments the amino acid is selected from the group consisting of leucine, glycine, alanine, proline, valine, isoleucine, methionine, tryptophan, phenylalanine, and combinations thereof, and in various embodiments the amino acid is an L-form amino acid such as, for example, L-leucine.

DETAILED DESCRIPTION

Figure 1:
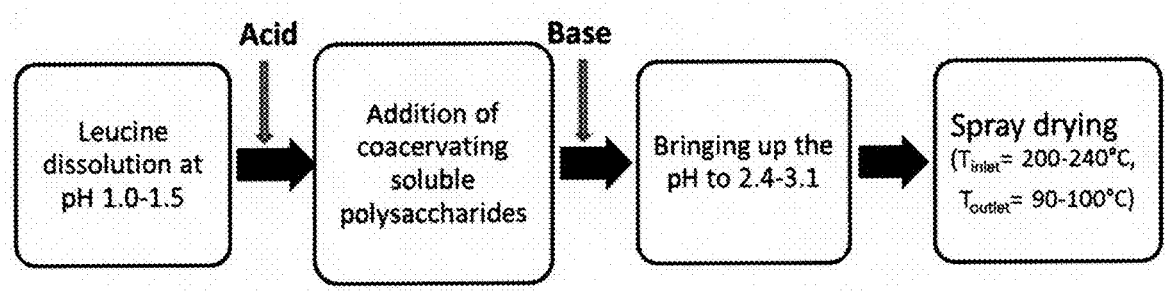
FIG. 1 is a general schematic of the coacervation process, using leucine as an example, according to the method of the invention.
Figure 2A:
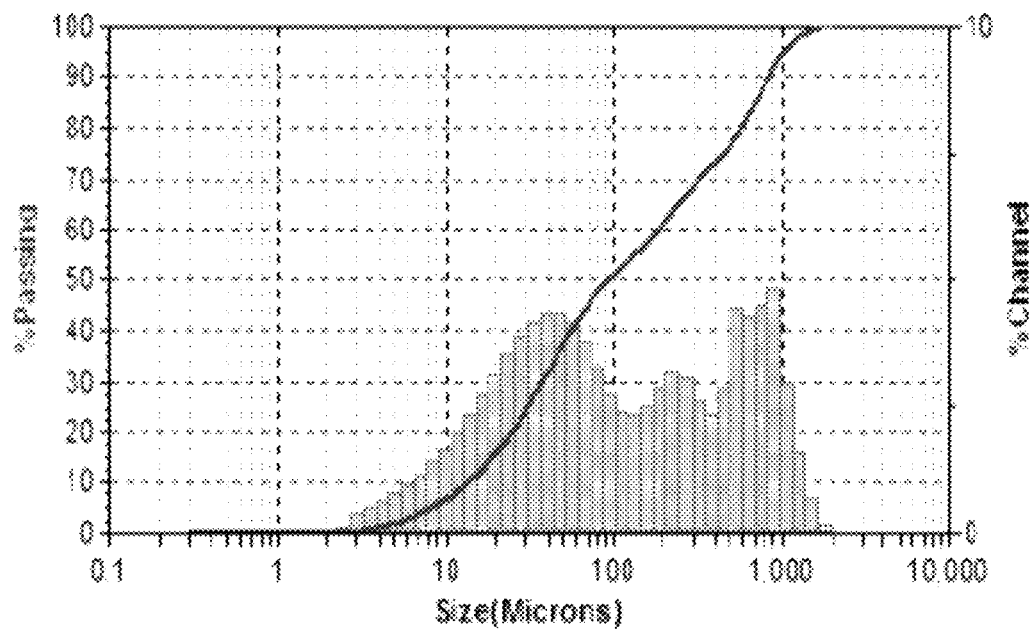
FIG. 2a is a graph of particle size of L-leucine (Shinestar)
Figure 2B:
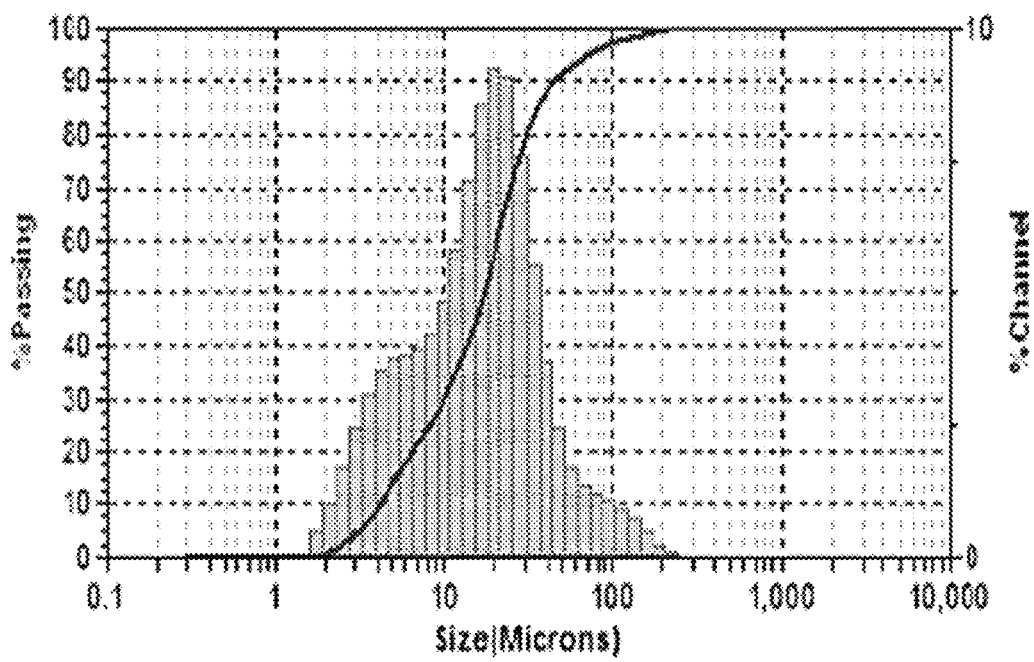
FIG. 2b is a graph of particle size of L-leucine coacervate made according to the method of the invention using L-leucine obtained from the same source.
Figure 3A:
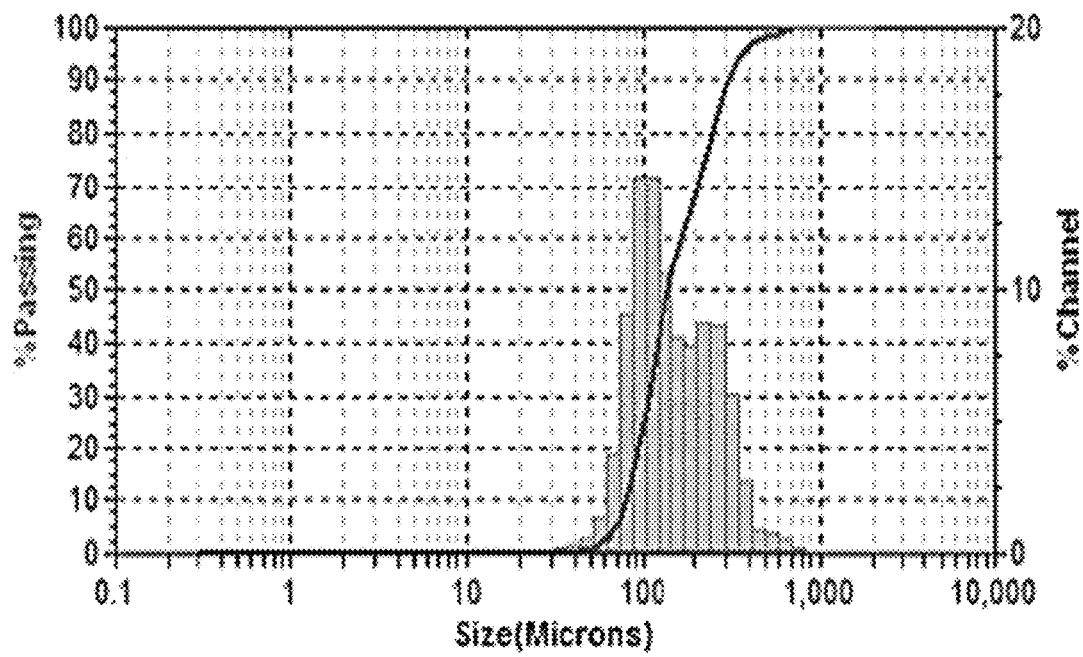
FIG. 3a is a graph of the particle size of L-leucine (Ajinomoto North America Inc.)
Figure 3B:
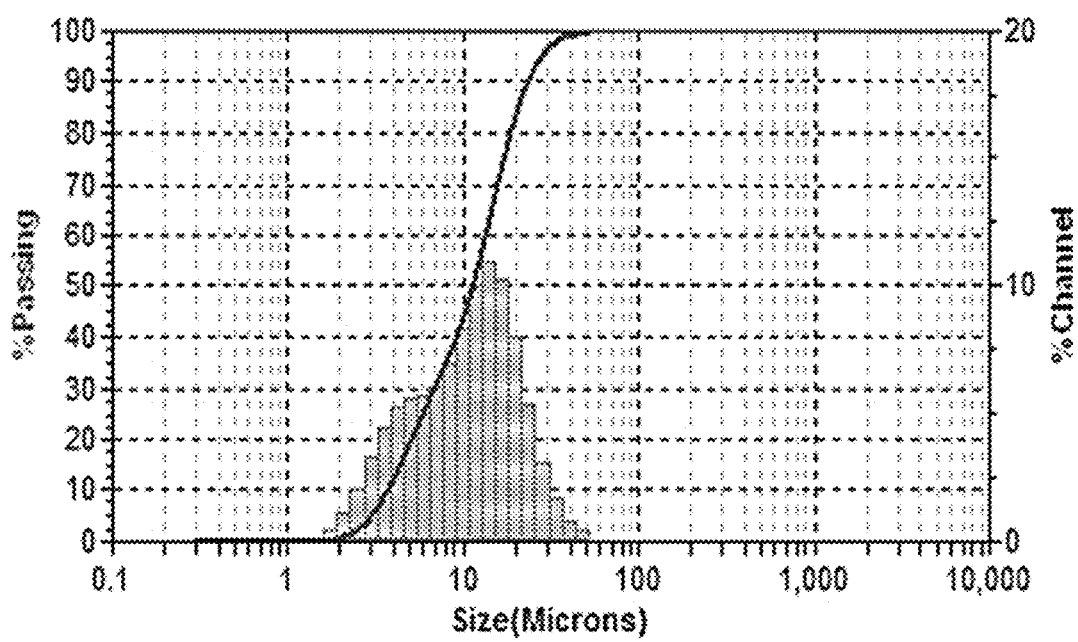
FIG. 3b is a graph of the particle size of L-leucine coacervate made according to the method of the invention using L-leucine obtained from the same source.
Figure 4:
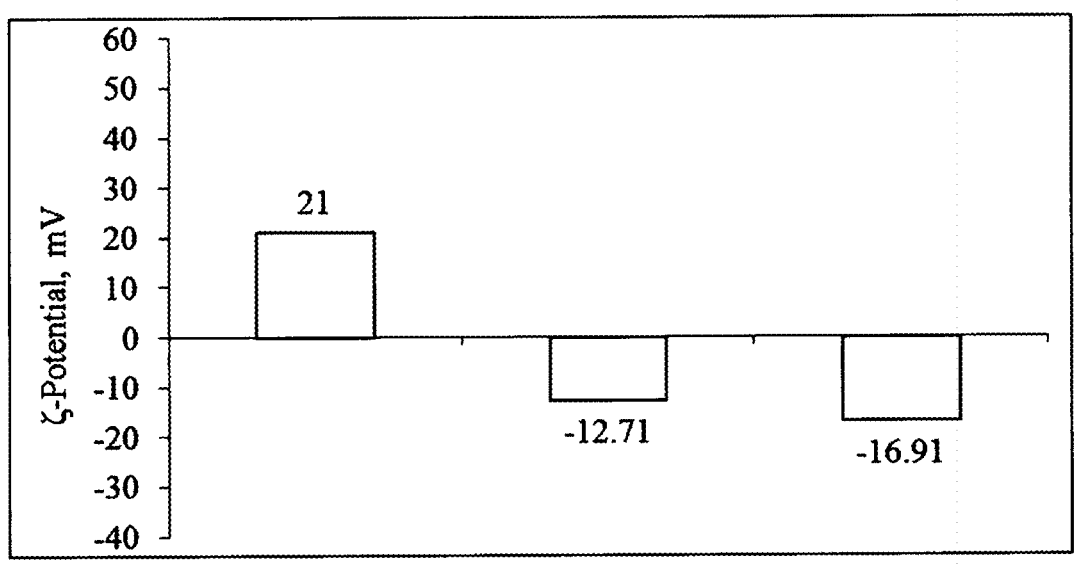
FIG. 4 is a graph of Zeta potential of: free leucine (at pH 1.0), coacervated leucine with 0.36 g/100 g of gum acacia (GA), and coacervated leucine with 6.67 g/100 g of gum acacia (GA), both at pH 2.3-2.5.
Figure 5:
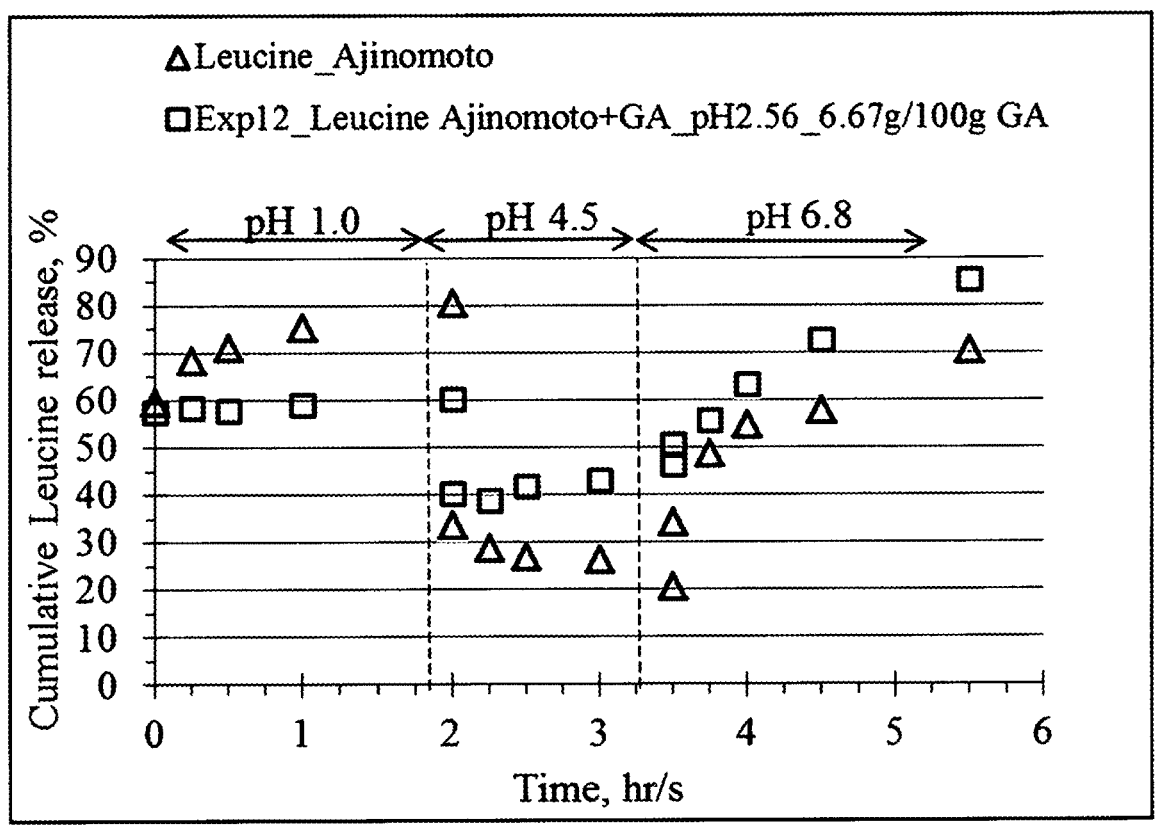
FIG. 5. is a comparison of the release profiles of leucine (Δ) and of leucine from a leucine/soluble polysaccharide coacervate (□), with leucine produced by Ajinomoto North America, Inc.
Figure 6:
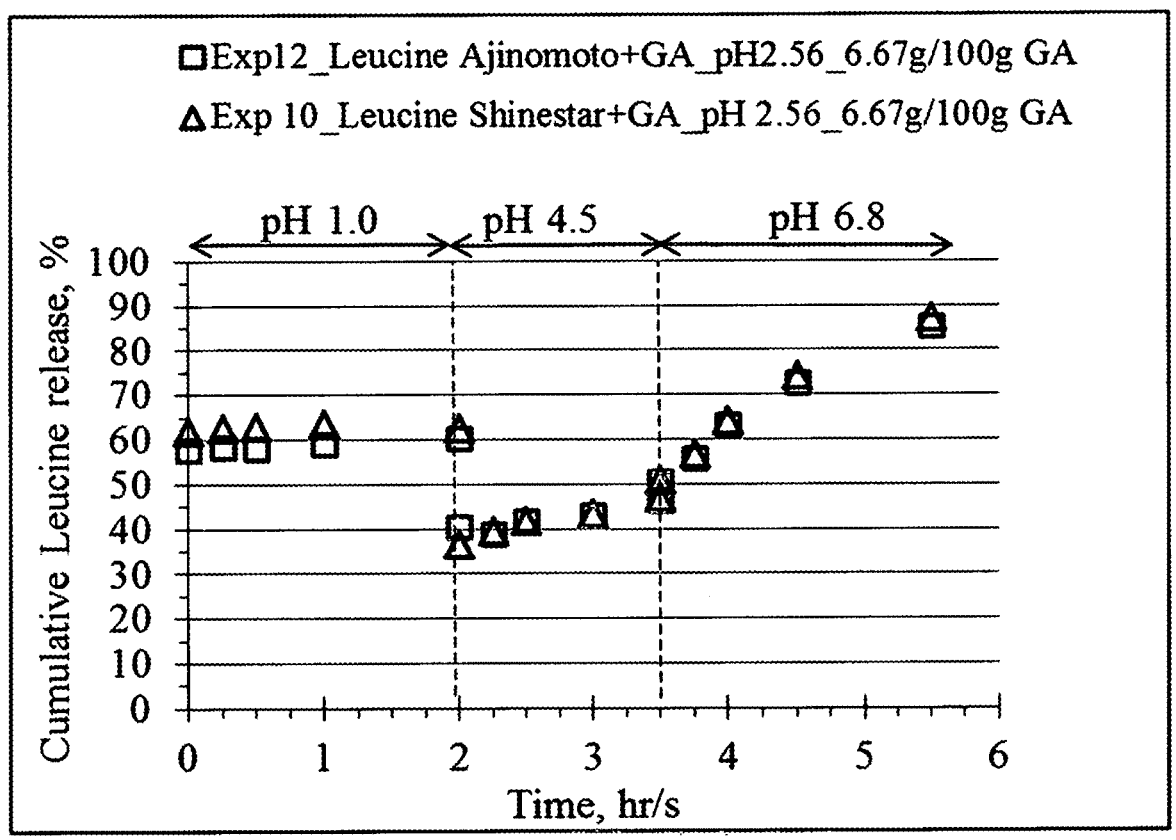
FIG. 6 is a comparison of the release profiles of leucine from a leucine/soluble polysaccharide coacervate, with leucine produced by two different manufacturers: Shinestar (◇) and Ajinomoto North America, Inc. (□).

The inventor has discovered that a coacervate, such as those which have previously been formed using larger molecules such as polypeptides and/or proteins with soluble polysaccharides such as gum acacia (gum Arabic), can be formed using isolated amino acid compositions. In various aspects, the amino acid comprises at least one non-polar amino acid such as, for example, leucine (which typically has a low solubility in water), to directly deliver leucine to the human and/or animal intestine, rather than by forming a coacervate of protein/polysaccharide and encapsulating leucine therein. By forming the coacervate using amino acid(s) (e.g., leucine) and a soluble polysaccharide such as, for example, gum acacia, the inventor has also developed a composition that provides controlled delivery of leucine, providing significantly more leucine release in the environment of the small intestine, where it can be absorbed into the bloodstream.

"Release" is used herein to mean the diffusion of the soluble form of a chemical into the surrounding medium, thus making it available for absorption. The surrounding media can be, for example, fluids within the various cavities of the gastrointestinal tract (i.e., stomach, duodenum, and small intestine). The soluble chemical can be one or more non-polar amino acids, such as leucine, glycine, alanine, proline, valine, isoleucine, methionine, tryptophan, phenylalanine, and/or combinations thereof.

The inventor has discovered that coacervates provide higher levels of amino acids such as leucine in a more concentrated form. Leucine, generally releases very quickly in the stomach, but is released much more slowly in that environment after being coacervated. Upon reaching the higher-pH environment of the small intestine, the coacervate provides a significantly higher rate/level of release than would a typical leucine product, such as a conventional capsule containing isolated leucine. The invention therefore provides a method for producing modified-release compositions comprising amino acids, such as non-polar amino acids exemplified by leucine. Leucine will be referred to herein both specifically, such as in the examples, and as a general representative of the group of non-polar amino acids. The method of the invention can be used to form coacervates of either polar or non-polar amino acids, or both, but the inventors have discovered that the efficiency of formation is higher when non-polar amino acids are used. Therefore, the non-polar amino acids are even more ideally suited for modified delivery applications using the method of the invention.

The invention therefore relates to a composition comprising at least one coacervate consisting essentially of one or more isolated amino acids and at least one soluble polysaccharide. In various aspects, the amino acid is leucine. In various aspects of the invention, the at least one soluble polysaccharide is gum acacia. In various embodiments of the invention, the coacervate comprises leucine at from about 45 to about 50 percent by weight of the coacervate.

In various aspects, a method for making a composition comprising an amino acid/soluble polysaccharide coacervate comprises the steps of (a) dissolving at least one soluble polysaccharide in water which has been preheated to from about 110 to about 122 degrees Fahrenheit and adjusted to a pH of from about 1.0 to about 1.5, to produce a soluble polysaccharide solution; (b) admixing at least one amino acid into the soluble polysaccharide solution, to produce an amino acid/polysaccharide admixture; and (c) adjusting the pH of the amino acid/polysaccharide admixture to from about 2.4 to about 3.1 to produce an amino acid/polysaccharide coacervate.

In various aspects, the method for making a composition comprising an amino acid/soluble polysaccharide coacervate comprises the steps of (a) dissolving at least one amino acid in water, adjusted to a pH of from about 1.0 to about 1.5, to produce an amino acid solution; (b) heating the amino acid solution to a temperature of from about 110 to about 122 degrees Fahrenheit; (c) admixing at least one soluble polysaccharide into the heated amino acid solution to produce an amino acid/polysaccharide admixture; and (d) adjusting the pH of the amino acid/polysaccharide admixture to from about 2.4 to about 3.1 to produce an amino acid/polysaccharide coacervate.

In various aspects, the method further comprises a step of drying the amino acid/polysaccharide coacervate. In various aspects, the at least one soluble polysaccharide is selected from the group consisting of gum acacia, pectin, soy-soluble polysaccharides, pea-soluble polysaccharides, and combinations thereof. In various aspects, the at least one soluble polysaccharide is gum acacia. In various aspects, the at least one amino acid is non-polar, in some embodiments the amino acid is selected from the group consisting of leucine, glycine, alanine, proline, valine, isoleucine, methionine, tryptophan, phenylalanine, and combinations thereof. In various embodiments, the amino acid(s) is/are L-form, such as L-leucine, for example.

The invention also relates to a method for making a leucine coacervate composition, the method comprising (a) dissolving leucine in water, which has been adjusted to a pH of from about 1.0 to about 1.1, to produce a leucine solution; (b) admixing into the leucine solution at least one soluble polysaccharide selected from the group consisting of gum acacia, pectin, soy-soluble polysaccharides, pea-soluble polysaccharides, and combinations thereof, to produce a leucine/polysaccharide admixture; (c) adjusting the pH of the leucine/polysaccharide admixture to from about 2.4 to about 3.1 to produce a leucine/polysaccharide coacervate. The method can further comprise a step (d), drying the leucine/polysaccharide coacervate.

As used herein, "coacervates" are spherical aggregates of colloidal droplets held together by electrostatic forces. According to Schmitt and Turgeon (Protein/polysaccharide complexes and coacervates in food systems, *Advances in Colloid and Interface Science* 167 (2011) 63-70), when proteins and polysaccharides form these complexes, they generally originate from electrostatic interactions between oppositely charged macromolecules. As they explain, the interaction between those macromolecules impacts coacervate formation, viscosity, etc. Coacervates formed between leucine-containing polypeptides and polysaccharides such as gum acacia have previously been described, and they have been suggested to be promising for delivery of leucine to the digestive system. However, the present invention can provide significantly higher amounts of leucine, can decrease the cost of providing leucine because it eliminates the need for the leucine-protein and/or polypeptide complex in previously-described coacervates, and, very importantly, delivers the leucine in a controlled-release form that targets delivery primarily to the intestine, where it is absorbed for use in the body.

Gum arabic (GA), obtained from the acacia tree (and therefore also referred to as "gum acacia"), is a branched polysaccharide with six carbohydrate moieties and one polypeptide moiety. GA is a weak polyelectrolyte with carboxylic groups that give it negative charge above pH 2.0. It is soluble in water and has low viscosity. The polypeptide fraction is predominantly hydroxyproline and serine and is covalently bound to the reducing end of the polysaccharide chains. Gulao, et al. (Complex coacervates obtained from peptide leucine and gum arabic: Formation and characterization interactions, *Food Chemistry* 194 (2016) 680-686) used a polypeptide to which leucine has been non-covalently bound and demonstrated that interactions between the polypeptide and GA could "produce insoluble precipitates, complexes, or coacervates, depending on the polysaccharide amount, pH, and salt concentration." As explained by Livney, (Livney, Y. D., Complexes and conjugates of biopolymers for delivery of bioactive ingredients via food, in *Delivery and Controlled Release of Bioactives in Foods and Nutraceuticals,* 2008, p. 234-250), "[c]omplex formation occurs between biopolymers exhibiting attractive interactions, including mainly electrostatic attraction between oppositely charged fixed groups on the polymers. However, other attractive interactions may also play important roles, e.g. hydrogen bonds, Van der Waals and hydrophobic interactions."

Compositions of the invention consist essentially of a first component consisting essentially of at least one amino acid, and a second component consisting essentially of at least one soluble polysaccharide. Soluble polysaccharides can be selected, for example, from the group consisting of pectin, maltodextrin, gum acacia (gum Arabic), soluble glucans such as, for example, β-glucans, chitosan sulfate, alginates, soy based soluble fiber, pea based soluble fiber, and combinations thereof. The inventor has found Gum acacia, soy soluble polysaccharide, and pea soluble polysaccharide to be particularly effective for forming coacervates with amino acids, especially leucine, in the method of the invention.

In the method of the invention, leucine is solubilized in solution by adjusting the solvent (e.g., water) to a pH of from about 1.0 to about 1.1. Soluble polysaccharide (SP) is added at a ratio of soluble polysaccharide to amino acid of from about 0.25 to about 0.6 amino acid/coacervating agent. The solution is admixed to homogeneity (i.e., lumps of SP should not be noticeable in the solution) and the pH is adjusted to from about 2.3 to about 2.5. At this pH, the low solubility amino acid (e.g., leucine) crystallizes. The percentage of amino acid (leucine) remaining in the coacervate with the SP will generally be from about 40 to about 65 percent (dry weight). At this point, the solutions will generally have a solids content of from about 8 to about 25, and even more preferably, from about 8.3 to about 24.9 percent. To produce a powder, the leucine/SP coacervate can be spray-dried, for example. Suitable conditions for spray-drying include an inlet temperature of from about 392° F. to about 464° F. (200-240° C.) and an outlet temperature of from about 194° F. to about 212° F. (90-100° C.).

Because leucine is present in the coacervate powder at from about 45 to about 50% by weight, the recommended dosage would be about from about 126 to about 140 mg of leucine coacervate per kg body weight (8.06-8.96 g per day for an average-size adult, for example).

Leucine is readily available from a variety of commercial sources, as are the variety of soluble polysaccharides that can be used to produce leucine coacervates according to the method of the invention. Compositions of the invention can be used in a variety of applications, such as powdered nutritional supplements, either alone or in combination with other nutritional ingredients, drink mixes, etc., or they may be used as ingredients in food and/or drink products. Given leucine's beneficial effects, leucine coacervates of the invention can be especially beneficial in products produced for athletes, with the significant amounts of leucine provided being used to build and repair muscle impacted by the effects of strenuous exercise. Leucine coacervates of the invention can also be incorporated into powdered nutritional supplements, protein bars, snack foods, and drink formulations, such as nutritional shakes, puddings, etc., to benefit elderly individuals who are at risk for muscle wasting, which can negatively impact overall health, decrease mobility, lead to balance issues, as well as other physical issues which can not only lead to illness, but also to injury. They can also be administered in the form of tablets, capsules and gummies, which are quite common types of solid dosage forms currently used in the nutraceutical market.

Coacervate compositions of the invention can also be dual-benefit compositions that provide the benefits of the one or more amino acids, as well as the benefits associated with the soluble polysaccharide. Many soluble polysaccharides are commonly referred to as "soluble fiber," and the benefits of soluble fiber are well-known. Certain soluble polysaccharides, such as β-glucans, for example, have well-documented benefits such as improving cholesterol levels and heart health, inhibiting tumor growth, reducing tumor proliferation, and preventing tumor metastasis. These polysaccharides have been shown to boost the immune response, and they have been used in therapeutic regimens as an adjuvant to cancer chemotherapy and radiotherapy. In cancer patients, increasing the amount of protein in a meal and by providing additional leucine has been found to stimulate muscle protein synthesis. In chronic obstructive pulmonary disease and cystic fibrosis, muscle protein synthesis can be stimulated by meals with specific dietary proteins and specific combinations of dietary essential amino acids, particularly leucine, so for these individuals, leucine coacervates of the present invention may be especially beneficial.

Coacervates formed from leucine-containing peptides, or leucine-containing peptides to which leucine has non-covalently been bound have been shown to be of larger particle size than the size of the starting material (Gulao, et al. (Complex coacervates obtained from peptide leucine and gum arabic: Formation and characterization interactions, *Food Chemistry* 194 (2016) 680-686), whereas coacervates of the present invention are of smaller particle size than the starting material. Since particle size can influence solubility, clarity of solutions into which the particles are solubilized, etc., leucine coacervates can also provide a greater variety of options for products into which formulators may want to incorporate supplemental leucine.

Where the term "comprising" is used, it should be understood that the components of the composition or the steps of the method to which the term is applied may also be described as "consisting essentially of" or "consisting of" those same components or steps, with the term "comprising" being used to describe the composition and/or the method in its/their broader scope. Where the phrase "consisting essentially of" is used, it should be understood that the transitional phrase "consisting essentially of" refers to the specified materials or steps and those materials or steps that do not materially affect the basic and novel characteristics of the invention. The invention will be further described by means of the following examples.

EXAMPLES

The pH of 550-1000 mL of water was lowered to 1.0-1.5 with HCl, or an acid blend of $H_3PO_4$ and HCl. To this, 6.6-23.8 g/100 g of L-leucine was added slowly under continuous stirring. Since leucine addition increased the pH slightly to pH 1.4-1.6, the pH was brought back to 1.0-1.1. Gum acacia or similar Soluble Polysaccharides (SP) (1.8-6.3 g/100 g) was added to the leucine solution by slow addition with continuous agitation. After all the lumps of SP/s were broken up and homogenously mixed, the final pH was adjusted to 2.4-3.1 with NaOH (12.5M), or KOH (12.5 M) solution. The blending process of SP/s was carried out at 110-122 F (~43-50° C.). The dispersion was stored overnight at 40-45° F. (4.5-7.2° C.). Just before spray drying, the dispersion was continuously stirred for 20 minutes. Spray-drying was performed with inlet temperature, 392-464° F. (200-240° C.) and outlet temperature of 194-212° F. (90-100° C.).

In some cases, SP/s was dispersed (1.8-6.3 g/100 g) into heated, acidified water (pH 1.0-1.5; 110-122 F (~43-50° C.)), and then leucine was slowly added to this solution under continuous stirring to create a dispersion. The pH of the dispersion was then adjusted to 2.4-3.1 by the addition of base.

Incorporation efficiency of leucine in the coacervate was calculated by dispersing the leucine/SP powder in RO water, 100 g/L. The mixture was centrifuged to separate the non-dissolved leucine in the residue from the dissolved leucine in the supernatant. The residue was again dissolved in same volume of fresh RO water. Both the supernatant and the residue were analyzed for leucine content using UPLC-UV (ultra-performance liquid chromatography with UV detection). Incorporation Efficiency (%) was measured as the ratio between the amount (g/100 g) of leucine in the supernatant plus residue, divided by the weight of powder taken for the dissolution study (g/100 g). The % incorporation after the spray-drying process was calculated to be 46%.

Release Study

The spray-dried leucine coacervate (100 mg of powder in 1 mL release medium) was dispersed in 20 mL PBS (0.3M) buffer. The pH was maintained at approximately 1.0. Release was assessed under continuous stirring. At various time points (0, 15 min., 30 min., 1 hr., 2 hr.), 1 mL of dispersion was taken out and washed at 13000 rpm for 5 min, and the same volume (1 mL) of fresh PBS buffer (of same pH) was added to the dispersion. The supernatant was subjected to UPLC. The residue was dispersed in 1 mL of fresh PBS buffer and vortexed. If any particles were seen floating in the tube, 1-2 drop of 6N HCl was added to it, then vortexed. This residue sample was also subjected to UPLC. The pH of the dispersion was then changed to 4.5, the sampling steps were repeated at time points 0, 15 min., 30 min., 1.5 hr. The pH of the dispersion was then changed to 6.8, repeating the sampling steps again at 0, 15 min., 30 min., 1 hr., and 2 hr.

There was very little variance between the leucine release profiles for coacervates produced from leucine obtained from different suppliers. The release profile of leucine from the leucine/GA coacervate was about 60-65% within 2 hours at pH 1.0. At pH 4.5 there was a slow release of about 7-12% at pH 4.5. After adjustment to pH 7.4, there was a sustained release of about 23-27% within 2 hrs. This indicates that a total of about 95-100% is released under conditions that simulate those of the digestive system. Furthermore, after leucine is incorporated into the coacervate, the release of leucine is a controlled release, being reduced by about 15-20% after 2-hours at pH 1.0. At pH 4.5, there is about a 20-26% increase in release after 1.5 hours, and about a 10-17% increase in release after 2 hours at pH 6.8.

Particle Size Analysis

Particle size was measured in microns, demonstrating that after the coacervate-forming process the leucine/gum arabic coacervate powder is 10 times smaller, with a narrower particle size distribution.

Zeta Potential Measurements

Zeta potential analysis was performed in on a NanoBrook ZetaPlus Zeta Plus instrument from Brookhaven Instruments. The uncoated leucine had a positive charge. Furthermore, after different concentrations (1.8-6.3 g/100 g) of SP were used, there was a reversal of surface charge having a negative zeta potential value of −13 to −17 mV, indicating that SP is coated on the leucine core.

What is claimed is:

1. A method for making a composition comprising an amino acid/soluble polysaccharide coacervate, the method comprising:
    (a) dissolving at least one amino acid in water, adjusted to a pH of from about 1.0 to about 1.5, to produce an amino acid solution;
    (b) heating the amino acid solution to a temperature of from about 110 to about 122 degrees Fahrenheit;

(c) admixing at least one soluble polysaccharide into the heated amino acid solution to produce an amino acid/polysaccharide admixture; and (d) adjusting the pH of the amino acid/polysaccharide admixture to from about 2.4 to about 3.1 to produce an amino acid/polysaccharide coacervate.

2. The method of claim 1 further comprising a step (e) drying the amino acid/polysaccharide coacervate.

3. The method of claim 1 wherein the at least one soluble polysaccharide is selected from the group consisting of gum acacia, pectin, soy-soluble polysaccharides, pea-soluble polysaccharides, and combinations thereof.

4. The method of claim 1 wherein the at least one soluble polysaccharide is selected from the group consisting of gum acacia, soy soluble polysaccharide, pea soluble polysaccharide, and combinations thereof.

5. The method of claim 1 wherein the at least one soluble polysaccharide is gum acacia.

6. The method of claim 1 wherein the at least one amino acid is non-polar.

7. The method of claim 1 wherein the amino acid is selected from the group consisting of leucine, glycine, alanine, proline, valine, isoleucine, methionine, tryptophan, phenylalanine, and combinations thereof.

8. The method of claim 1 wherein the amino acid is L-leucine.

9. A method for making a composition comprising an amino acid/soluble polysaccharide coacervate, the method comprising:

(a) dissolving at least one soluble polysaccharide in water which has been preheated to from about 110 to about 122 degrees Fahrenheit and adjusted to a pH of from about 1.0 to about 1.5, to produce a soluble polysaccharide solution;

(b) admixing at least one amino acid into the soluble polysaccharide solution, to produce an amino acid/polysaccharide admixture; and (c) adjusting the pH of the amino acid/polysaccharide admixture to from about 2.4 to about 3.1 to produce an amino acid/polysaccharide coacervate.

10. The method of claim 9 further comprising a step (e) drying the amino acid/polysaccharide coacervate.

11. The method of claim 9 wherein the at least one soluble polysaccharide is selected from the group consisting of gum acacia, pectin, soy-soluble polysaccharides, pea-soluble polysaccharides, and combinations thereof.

12. The method of claim 9 wherein the at least one soluble polysaccharide is selected from the group consisting of gum acacia, soy soluble polysaccharide, pea soluble polysaccharide, and combinations thereof.

13. The method of claim 9 wherein the at least one soluble polysaccharide is gum acacia.

14. The method of claim 9 wherein the at least one amino acid is non-polar.

15. The method of claim 9 wherein the amino acid is selected from the group consisting of leucine, glycine, alanine, proline, valine, isoleucine, methionine, tryptophan, phenylalanine, and combinations thereof.

16. The method of claim 9 wherein the amino acid is L-leucine.

* * * * *